United States Patent [19]
Mortensen

[11] 3,934,273
[45] Jan. 27, 1976

[54] PROSTHETIC LIMB WITH WEIGHT-RESPONSIVE JOINT LOCK

[76] Inventor: La Vaughn L. Mortensen, 10533 San Anselmo, South Gate, Calif. 90280

[22] Filed: Jan. 20, 1975

[21] Appl. No.: 542,217

[52] U.S. Cl. ............................................ 3/27; 3/28
[51] Int. Cl.² ........................ A61F 1/04; A61F 1/08
[58] Field of Search ............................... 3/22–29, 2

[56] References Cited
UNITED STATES PATENTS

| | | | |
|---|---|---|---|
| 3,694,823 | 10/1972 | May | 3/27 |
| 3,723,997 | 4/1973 | Kolman | 3/27 |
| 3,863,274 | 2/1975 | Glabiszewski | 3/27 |

FOREIGN PATENTS OR APPLICATIONS

| | | | |
|---|---|---|---|
| 1,169,464 | 11/1969 | United Kingdom | 3/27 |

Primary Examiner—Ronald L. Frinks
Attorney, Agent, or Firm—Dominick Nardelli

[57] ABSTRACT

In a knee structure for a prosthetic limb which allows the shin portion to pivot with respect to the thigh portion about an axle fixed to the shin portion and passing through aligned openings in the thigh portion, a brake-band is disposed slightly less than 360° around the axle, wherein the lower end of the band is pivotably anchored around a pin fixed to the thigh portion and disposed parallel to the axle. The upper end of the band responds to the relatively downward motion of the thigh portion when weight is supported thereby to cause a braking action between the band and axle. A drag adjustment means is provided wherein the thigh portion bears against the upper band and, while the aligned openings in the thigh portion restrain any downward movement of the axle.

9 Claims, 6 Drawing Figures

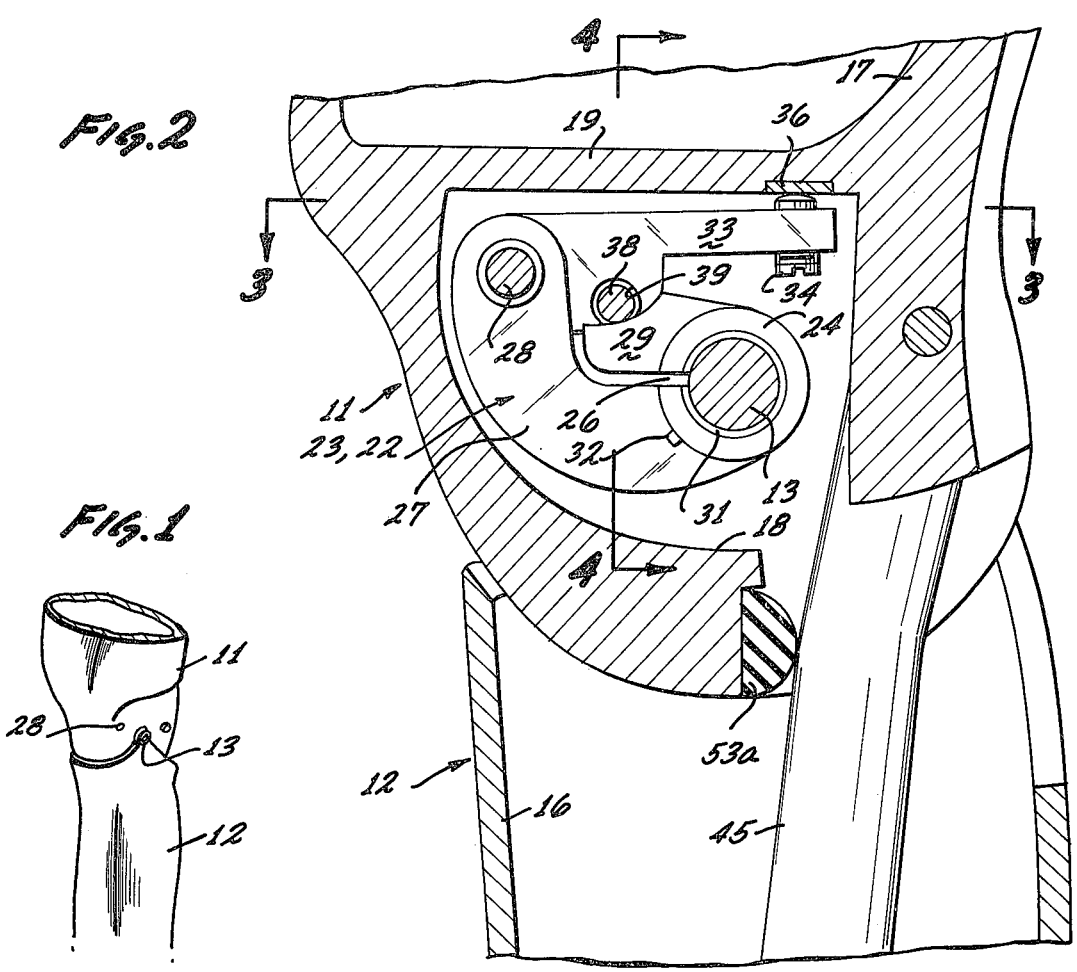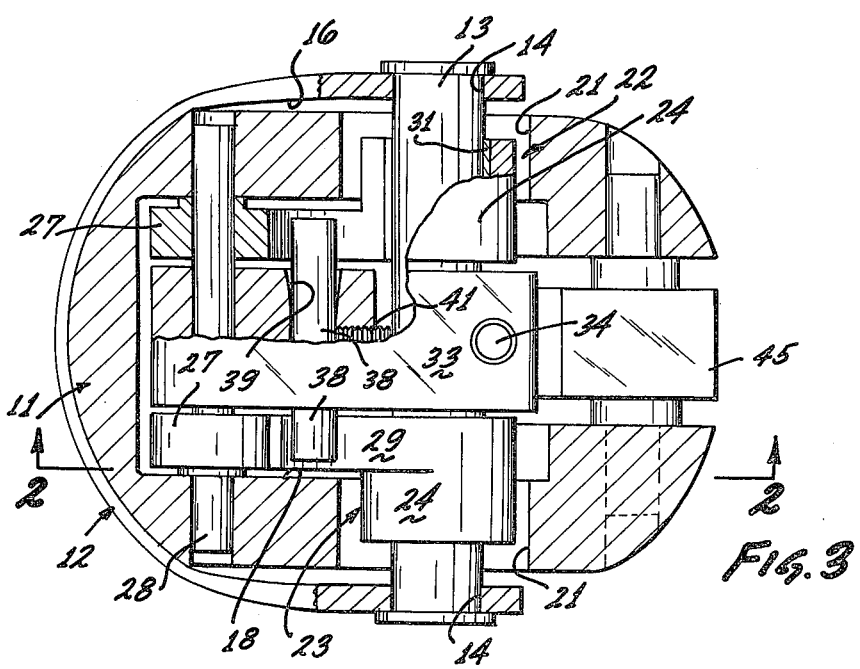

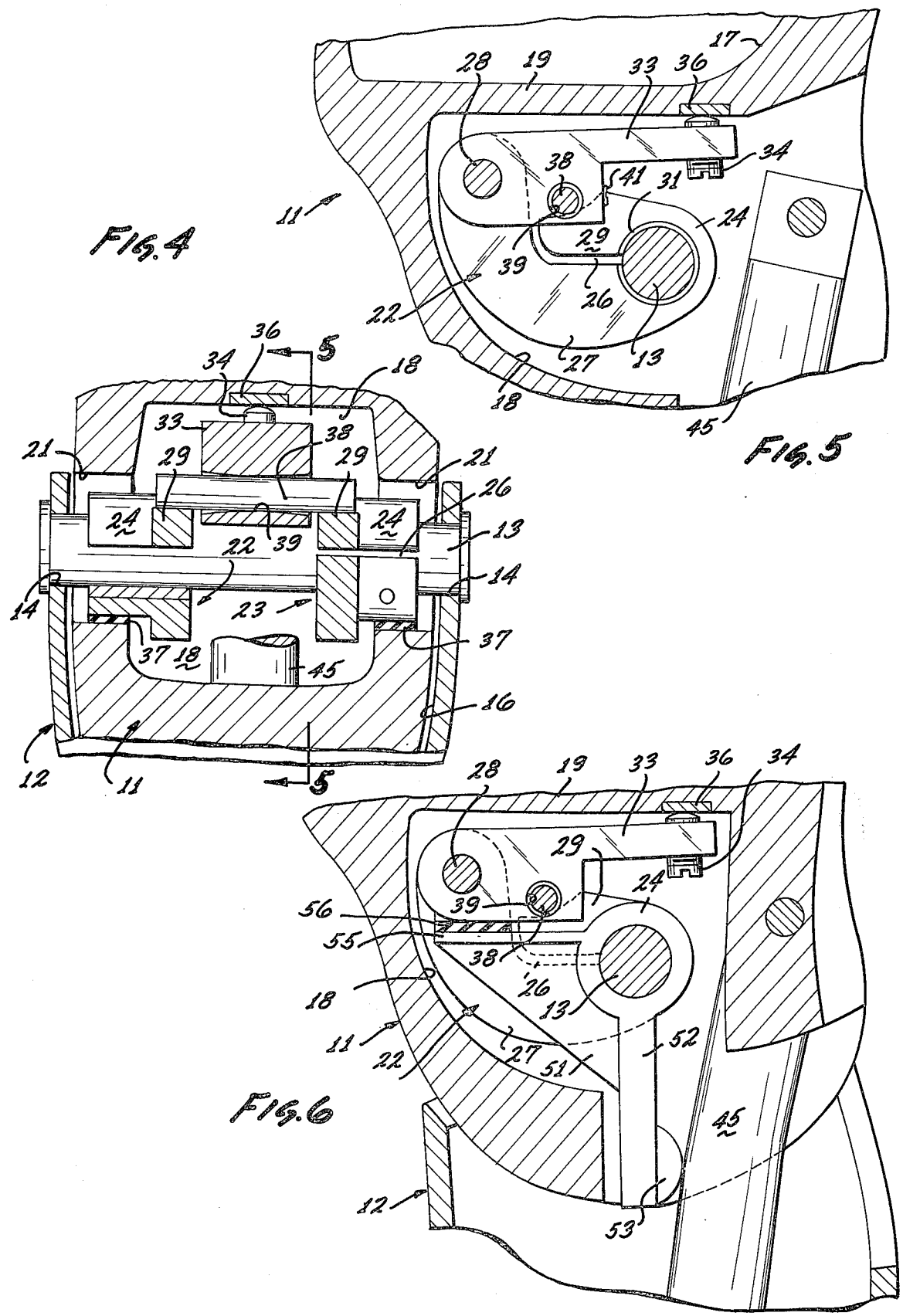

3,934,273

PROSTHETIC LIMB WITH WEIGHT-RESPONSIVE JOINT LOCK

FIELD OF THE INVENTION

The present invention relates to a prosthetic limb and, more particularly, to a pivotable mechanism thereof, with a means for braking.

BACKGROUND OF THE INVENTION

Prosthetic or artificial limbs have been designed in many ways, and each way is calculated to simulate more closely the motion of a natural limb. However, at times, this appears to be an impossibility because of the many functions our Great Creator compacted within a relatively small package. Therefore, man can only hope to approach the function of the natural limb. Although U.S. Pat. No. 3,723,997 teaches a useful method of providing braking action within an artificial knee, like all human endeavors, these teachings could also stand improvement. One drawback of the prior art is that the mechanism is relatively noisy because "play" is required between moving parts to allow relatively free motion, when braking is not required. Also, separate additional elements are provided to adjust drag.

OBJECTS OF THE INVENTION

An object of this invention is to provide a simple, smooth operating, pivotable structure for a prosthetic limb which can be locked in any angular position as the limb supports weight.

Another object is to provide a knee structure for a prosthetic leg, having a means for locking the knee whenever weight is supported by the leg, and moves freely and quietly to the straightened position.

Another object of this invention is to provide a means to prevent brake lock-up when the shin is fully extended and the weight supported on the toes thereof so that easy flexion is available on take off.

Another object of this invention is to provide a simple, adjustable drag means on a pivotable assembly for a prosthetic limb.

These and other objects and features of advantage will become more apparent after studying the following detailed description of the preferred embodiment of the invention, together with the appended drawings.

BRIEF DESCRIPTION OF THE DRAWINGS

FIG. 1 is a pictorial representation of a typical prosthetic limb or leg, employing my novel, pivotable joint, with a weight-activated brake means.

FIG. 2 is a sectional view of the joint taken on line 2—2 of FIG. 3 and in the direction of the arrows.

FIG. 3 is a sectional and broken-away view of the joint taken on line 3—3 of FIG. 2 and in the direction of the arrows.

FIG. 4 is a sectional view taken on line 4—4 of FIG. 2, also in the direction of the arrows.

FIG. 5 is a sectional view similar to FIG. 2, but taken on line 5—5 of FIG. 4.

FIG. 6 is a sectional view similar to FIG. 2 showing a means for releasing the brake although weight is supported.

DETAILED DESCRIPTION OF THE DRAWINGS:

FIG. 1 shows a prosthetic leg incorporating my invention, and there is shown a thigh portion 11 and a shin portion 12, which pivot relative to each other about an axle or shaft 13. The axle 13 is disposed suitably fixed in any convenient manner to the shin portion 12 through suitable aligned bores 14 (FIG. 4). The shin portion 12 has a well 16 (FIG. 4) extending down through the top thereof, and bores 14 are formed in the opposing walls of the well. The lower end of the thigh portion 11 extends down into the well 16, as shown.

The thigh portion also has a well 17 (FIG. 2) which is separated from a cavity 18 by a wall 19 which is preferably disposed substantially normal to the axis of the thigh portion. The axle 13 also passes through aligned holes 21 (FIG. 4) formed in the thigh portion, which holes communicate with the cavity 18. Around the axle 13 is disposed a pair of brake bands 22 and 23. The bands 22 and 23 are generally U-shaped and each consists of a boss 24 slitted axially parallel by a slit 26. The bosses 24 are made sufficiently thick and of metal to have sufficient spring-back elasticity for reasons that will become apparent hereinafter. The bottom or lower portion of each boss 24 is made integral with an arm 27, having its end pivotably engaging a pin 28 disposed across the cavity 18, as shown more clearly in FIG. 3. The upper portion of each boss 24 is made integral with an upper lug 29, as shown. To insure smooth drag between the axle 13 and the bands 22 and 23, a suitable slitted bushing 31 is provided between each boss 24 and the axle 13. As, for example, the axle is made of steel and the bushings are made of standard sintered self-lubricating bronze. The bushing 31 is held fixed with respect to the boss 24 by means of a rivet 32. The brake bands 22 and 23 and axle 13 are inherently disposed pivotable about pin 28 for obvious reasons. Since the axle 13 passes loosely through holes 21, the thigh portion 11 and the shin portion 12 will pivot with respect to each other as long as the bands 22 and 23 are loosely disposed around the axle 13. However, as will be explained hereinafter, suitable means are provided to remove all play between the thigh and shin portions and place a predetermined rotation drag force around the axle.

Now, one can see that if the wall 19 can be made to bear against the lugs 29 of the brake bands and the axle 13 can be made to bear against the shin portion 12, a braking or drag force can be formed to prevent pivotable motion between the thigh and shin portions. To amplify the braking force so that more than the force which the wearer is capable of applying is used to lock the joints, a lever 33 is provided. The lever 33 has one end pin-connected to pin 28 and is disposed between the brake bands substantially parallel to wall 19. The other end of lever 33 is made to engage the wall 19 through an adjustment screw 34. A metallic bearing plate 36 is disposed on wall 19 for the screw 34 to bear against. When the limb is lifted off the ground, the axle is prevented from dropping or moving away from wall 19 by suitable bearing pads 37 (FIG. 4), bonded to the lower periphery of each hole 21 below the bosses 24, as shown in FIG. 4. A dowel bar 38 is provided, as shown, passing through an opening 39 in lever 33 to engage both lugs 29 of the respective brake bands. The opening 39 is made smaller at the center than at the ends, so that the bar 38 can pivot a limited amount about a horizontal axis. This insures that equal force is being applied to the respective brake bands. The bar 38 is held in place by a screw or pin 41, as shown in FIG. 3.

To apply a predetermined drag on a brake band 23 so that the shin portion is prevented from swinging like a pendulum, the screw 34 can be turned any desired amount. Since the axle 13, but more particularly the bosses 24, are prevented from moving downward by pads 37, the upper lugs 29 are urged toward the respective arms 27, as the screw 34 is turned into the lever 33 and against the bearing plate 36. Therefore, the bushings 31 are squeezed against the axle 13. This feature of allowing the pads 37 to bear against the bosses 24 allows removal of the axle 13 without disturbing the drag. To provide further dependable operation of the knee joint, the line of contact between pin 38 and lugs 29 is parallel to and substantially in the same plane as defined by the axes of both the pin 28 and axle 13.

As in all prosthetic limbs, the thigh and shin portions 11 and 12 pivot to a bent position at the command or action of the user. Although the thigh and shin portions could assume the extended position by gravatational action, the two portions 11 and 12 are made to return to their right position by a standard means 45, which is well known in the art. (See U.S. Pat. No. 3,316,558). Means 45 act something like a compression spring which returns the shin portion to the aligned position with the thigh against the drag which was formed by adjustment in turning screw 34. Because the upper ends of both brake bands are the ones which are free to move, the pivoting of the shin portion back to its aligned position prevents the wrapping of the brake band around the axle and prevents inadvertent application of a braking force.

In use, the brake is applied whenever the wearer places weight on the prosthetic leg, the weight bearing on the leg causes the bosses 24 to lift slightly off the respective pads 37. Since lever 33 is held relatively fixed to the thigh portion 11, the arm 27 is moved toward lug 29 to squeeze the bosses 24 around the axle. This braking action, as in U.S. Pat. No. 3,623,997, can be applied by the wearer when the knee is in any angular position. When the wearer lifts his leg, as when walking, the knee is free to bend. In other words, the brake band encircles the axle 13 in a self-energizing direction with a flexion rotation the produce greater resistance to flexion than to extension rotation.

Referring to FIG. 6, a means is shown to release the brake action when the shin is fully extended and supporting weight. As mentioned, FIG. 6 is substantially the same view as FIG. 2 but with the means including a bell crank 51 added in a certain way so that the brake is released while supporting weight when the wearer has the limb positioned with the shin 12 in the fully extended position, for example, when simulating a toe stand position. In this position, the standard means 45 bears against an arm 52 on the bell crank 51 and more particularly to a resilient bumper 53. As shown, the thigh portion 11 is so shaped to allow arm 52 to depend down through the cavity 18. A bumper 53a (FIG. 2), on the thigh 11 is removed to be placed on the arm 52. In the embodiment shown in FIG. 6, the bell crank 51 is disposed between the brake bands 22 and 23 and pivots about axle 13. A horizontal arm 55 is disposed to bear against the lever 33, preferably under the pin 28 when the wearer simulates a toe stance on this limb. To prevent noise or chatter, a resilient pad 56 is cemeted to the upper side of arm 55. One can see that as the shin portion 12 tends to rotate clockwise about axle 13, the standard means 45 also urges the bell crank 51 clockwise, but actually the bell crank 51 tends to pivot about resilient pad 56 rotating the brake bands 22 and 23 clockwise about pin 28, thereby disengaging dowel bar 38 from the upper lugs 29. Now, when the wearer kicks off, as to take a step, the shin 12 can immediately flex counter-clockwise.

If a limb is designed without the standard means 45, a bell crank means (not shown) similar to the bell crank 51 shown could be used. However, the bell crank would have a depending arm corresponding to arm 52 which would engage the shin portion 12 inside of the well 16, preferably at the rear thereof. Now, the bell crank would pivot in unison with the shin portion.

Although the preferred embodiments of my invention have been described, one skilled in the art, after studying the above detailed description thereof, can devise other embodiments without departing from the spirit and scope of my invention. Therefore my invention is not to be considered limited to the disclosed embodiment, but includes all embodiments falling within the scope of the appended claims.

I claim:
1. A pivotable mechanism for a prosthetic limb, comprising:
   a first portion with a cavity formed at one end thereof;
   a second portion with a well formed at one end to allow said one end of said first portion to pivot freely therein;
   an axle fixed to said second portion and disposed across said well;
   a pin fixed to said first portion and disposed across said cavity and substantially parallel to said axle;
   said axle being disposed to extend also across said cavity;
   at least one U-shaped brake band disposed around said axle and within said cavity, with the one end of the brake band remote from said first portion engaging said pin, and
   first means are provided for causing said first portion to contact the other end of said brake band to cause the ends thereof to move toward each other whenever said first portion is urged toward said second portion;
   said first means comprises:
   a lever pivotably connected to said pin and disposed to extend substantially parallel to said brake band on the side of the band remote from said second portion;
   said lever having its end disposed to make contact with the wall of said cavity, which wall is remote from said second portion;
   said lever having disposed between its end a contact means for making contact with said other end of said brake band;
   said contact means is substantially in the same plane as defined by the axes of said pin and axle.
   a threaded screw disposed in the end of said lever to make contact with said wall; and
   said first portion having a pair of holes formed in opposing walls of said cavity to allow said axle to pass through said pair of holes, whereby said axle is capable of bearing against the periphery of said pair of holes as said screw is tightened to allow adjustment of the drag force as produced by said brake band.

2. A pivotable mechanism for a prosthetic limb, comprising:
   a first portion with a cavity formed at one end thereof;

a second portion with a well formed at one end to allow said one end of said first portion to pivot freely therein;

an axle fixed to said second portion and disposed across said well;

a pin fixed to said first portion and disposed across said cavity and substantially parallel to said axle;

said axle being disposed to extend also across said cavity;

at least one U-shaped brake band disposed around said axle and within said cavity, with the one end of the brake band remote from said first portion engaging said pin, and first means are provided for causing said first portion to contact the other end of said brake band to cause the ends thereof to move toward each other whenever said first portion is urged toward said second portion;

said first means comprises:

a lever pivotably connected to said pin and disposed to extend substantially parallel to said brake band on the side of the band remote from said second portion;

said lever having its end disposed to make contact with the wall of said cavity, which wall is remote from said second portion;

said lever having disposed between its end a contact means for making contact with said other end of said brake band;

a second U-shaped brake band disposed around said axle with said lever disposed between said bands;

said one end of said second band remote from said first portion also engaging said pin;

said contact means comprising said lever having an opening disposed substantially parallel to said pin; and a dowel bar extending through the said opening and making contact at each end of said bar with the other end of each of said brake bands, respectively.

3. The mechanism of claim 2 wherein said bar and said opening are of a size so that said bar wobbles therein to cause an even braking force between said bands.

4. The mechanism of claim 3 wherein the region of contact, between said bar and the other ends of said bands, lies substantially in a plane as defined by the axes of said pin and axle.

5. The mechanism of claim 4 wherein:

a threaded screw is disposed in the end of said lever to make contact with said wall; and said first portion has a pair of holes formed in opposing walls of said cavity to allow said axle to pass through said pair of holes, whereby said axle is capable of bearing against the periphery of said pair of holes as said screw is tightened to allow adjustment of the drag force as produced by said brake band.

6. The mechanism of claim 11 wherein:

a means is included responsive to the extension action of said second portion to engage said lever under said pin so that the ends of the brake bands separate although said first portion is being urged toward said second portion.

7. The mechanism of claim 6 wherein said means includes:

a bell crank pivotably disposed about said axle and having a first and second arms disposed at an angle to each other;

said first arm depending from said axle and disposed to engage said second portion;

said second arm disposed to extend under said pin so that as said second portion returns to its extended position, said pin is lifted to disengage the braking action although the first and second portions are being urged toward each other.

8. A pivotable mechanism for a prosthetic limb, comprising:

a first portion with a cavity formed at one end thereof;

a second portion with a well formed at one end to allow said one end of said first portion to pivot freely therein;

an axle fixed to said second portion and disposed across said well;

a pin fixed to said first portion and disposed across said cavity and substantially parallel to said axle;

said axle being disposed to extend also across said cavity;

at least one U-shaped brake band disposed around said axle and within said cavity, with the one end of the brake band remote from said first portion engaging said pin, and first means are provided for causing said first portion to contact the other end of said brake band to cause the ends thereof to move toward each other whenever said first portion is urged toward said second portion;

second means responsive to the extension action of the second portion to lift said pin so that the ends of the brake band separate although said first portion is being urged toward said second portion.

9. The mechanism of claim 8 wherein said means includes:

a bell crank pivotably disposed about said axle and having a first and second arms disposed at an angle to each other;

said first arm depending from said axle and disposed to engage said second portion;

said second arm disposed to extend under said pin so that as said second portion returns to its extended position, said pin is lifted to disengage the braking action although the first and second portions are being urged toward each other.

* * * * *